United States Patent [19]

Goldberg

[11] 4,000,745

[45] Jan. 4, 1977

[54] ELECTRICAL LEADS FOR CARDIAC STIMULATORS AND RELATED METHODS AND MEANS

[76] Inventor: Edward M. Goldberg, 26 Crescent Drive, Glencoe, Ill. 60022

[22] Filed: Aug. 5, 1968

[21] Appl. No.: 750,218

[52] U.S. Cl. .......................... 128/418; 128/419 P; 339/67; 339/108 R
[51] Int. Cl.² .......................................... A61N 1/04
[58] Field of Search ............... 128/404, 418, 419 P; 339/67, 96, 108 R

[56] References Cited

UNITED STATES PATENTS

| 3,216,424 | 11/1965 | Chardack | 128/418 |
|---|---|---|---|
| 3,243,755 | 3/1966 | Johnston | 339/67 X |
| 3,253,595 | 5/1966 | Murphy, Jr. et al. | 128/418 X |
| 3,367,339 | 2/1968 | Sessions | 128/418 |
| 3,416,533 | 12/1968 | Fisher et al. | 128/404 |
| 3,416,534 | 12/1968 | Quinn | 128/418 |
| 3,472,234 | 10/1969 | Tachick | 128/418 |
| 3,485,247 | 12/1969 | Ackerman | 128/418 |

Primary Examiner—William E. Kamm
Attorney, Agent, or Firm—Hume, Clement, Brinks, William, Olds & Cook Ltd.

[57] ABSTRACT

The electrical leads for cardiac stimulators comprise an insulated electrical conductive section and a lead-in securing section including a helical member which may be screwed into the heart muscle. Preferably, there is interposed between these two sections a non-insulated electrical conducting section which becomes embedded in the heart upon insertion of the electrical lead. If there is any breakage between the lead-in securing section and the rest of the electrical lead, electrical impulses are still supplied to the heart by the cardiac stimulator.

An insertion tool is provided to attach the electrical lead to the heart.

25 Claims, 7 Drawing Figures

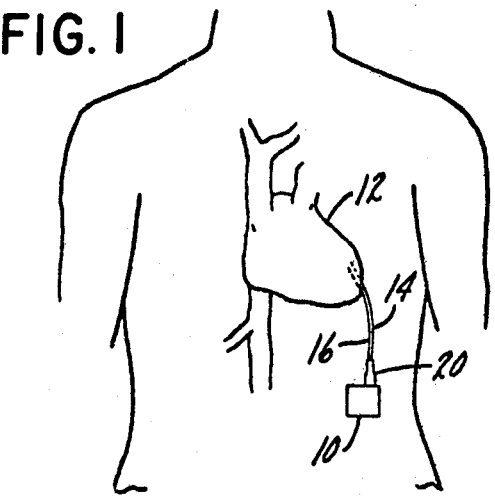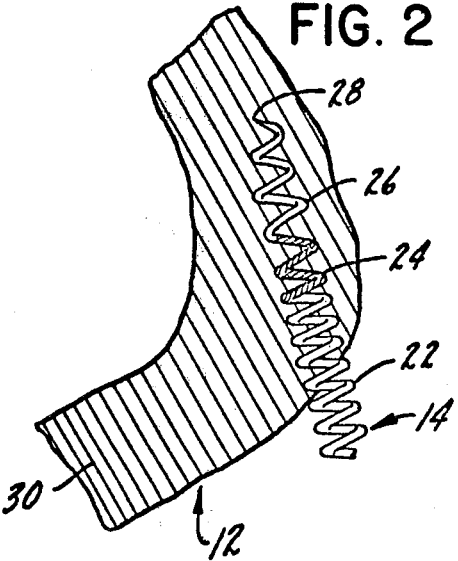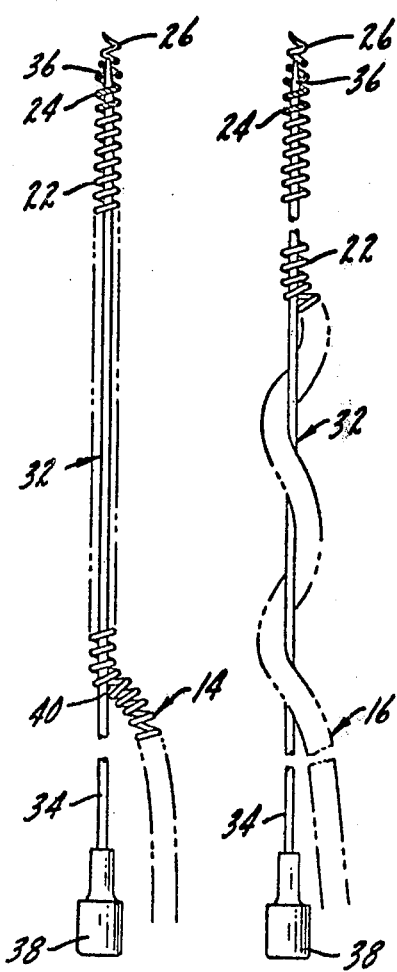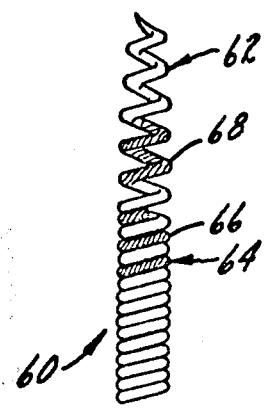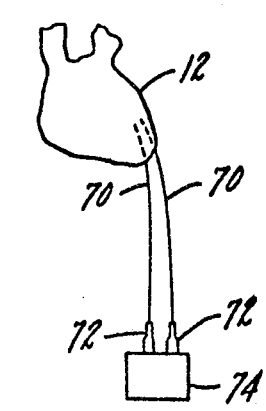

ELECTRICAL LEADS FOR CARDIAC STIMULATORS AND RELATED METHODS AND MEANS

This invention relates to methods and means for attaching a pacemaker or cardiac stimulator to the heart of animals and humans. It also relates to a cardiac stimulator system for S-A node heart blockage and a method for resisting coronary insufficiency.

The beat of human and animal hearts is controlled by electrical impulses entering the atrium and passing through to the ventricles. When the travel of these electrical impulses from the atrium to the ventricles is partially or totally impeded this condition is referred to as a "heart block". For some time heart blocks have been corrected by attaching "cardiac stimulators", small generators of electrical impulses, through electrical leads to the malfunctioning heart.

Cardiac stimulators have been used to pace the heart in synchronous and non-synchronous manners. In synchronous pacing suitable equipment is connected to the atrium to pick up the beat of the atrium. This electrical beat is coordinated with electrical impulses sent by a cardiac stimulator attached to the ventricles to achieve "synchronous" beating between the atrium and the ventricles.

In non-synchronous pacing the cardiac stimulator is merely attached to the ventricle and the beating of the ventricles and atrium is not in complete harmony. The efficiency of the heart is reduced in non-synchronous pacing approximately 20%, but since it requires fewer attachments to the heart non-synchronous pacing has been the most commonly used pacing system.

Heretofore a thoracotomy was commonly required to attach a cardiac stimulator to the heart and the electrical leads were sutured into electrical contact with the heart. This technique has numerous disadvantages. Firstly, a thoracotomy, which requires a large incision in the chest or thorax, is drastic surgery and has a relatively high mortality rate. Secondly, suturing the electrical leads into the electrical contact with the heart causes severe trauma to the heart, which it is desirable to minimize.

An intravenous connection has also been used to attach electrical leads of a cardiac stimulator to the heart. In this technique the electrical lead is passed through a vein into the heart where it is held by fibrilla located in close proximity to the heart valve through which the lead is passed. There are, however, many disadvantages to this technique also, including: the possibility of damage to the vein during insertion, such as vein perforation; the failure to securely attach the electrical lead to the heart; and the possibility of perforating the heart wall with the electrical lead during insertion or after attachment has been completed.

It is therefore desirable to provide methods and means for attaching a cardiac stimulator to the heart of an animal or human which do not require a thoracotomy, have less traumatic effect upon the heart and securely attach the electrical leads to the heart.

It is therefore an object of the present invention to provide an electrical lead for a cardiac stimulator which may be securely attached to the heart of an animal or human without the trauma caused by suturing an electrical lead onto the heart.

It is a further object to provide an electrical lead for a cardiac stimulator which may be attached to the heart through less drastic surgical procedures than a thoracotomy.

It is another object to provide an electrical lead for a cardiac stimulator which may be easily, yet firmly, attached to the heart.

It is yet another object to provide an improved electrical lead utilizing an insertion tool for securing the lead to the heart.

It is another object to provide a cardiac stimulator system which is corrective of S-A node blockage.

Other objects, features and advantages of the present invention will be apparent from the following detailed description taken in conjunction with the accompanying drawings in which:

FIG. 1 is a diagrammatic view of a cardiac stimulator attached to a human heart through electrical leads embodying the features of the present invention;

FIG. 2 is a partially cross-sectional, enlarged fragmentary view of the human heart with the electrical lead shown in FIG. 1 attached thereto;

FIG. 3 is a fragmentary, enlarged view of the electrical lead shown in FIG. 1 with an insertion tool embodying the features of the present invention utilized to attach the electrical lead to the heart;

FIG. 4 is a fragmentary, enlarged view of the insertion tool illustrated in FIG. 3 during another embodiment of the present invention;

FIG. 5 is a partially cross-sectional, enlarged view of an electrical lead constituting another embodiment of the present invention;

FIG. 6 is an enlarged fragmentary view of an electrical lead constituting still another embodiment of the present invention; and FIG. 7 is a diagrammatic view of a cardiac stimulator system embodying another feature of the present invention.

Referring now to FIG. 1 there is illustrated diagrammatically a cardiac stimulator 10 connected to a heart 12 of a human through electrical leads 14 and 16 embodying the features of the present invention. Each of the electrical leads 14 and 16 have one end securely attached to the heart 12, and their opposite ends attached to a single electrical plug 20, which is disconnectably attached to the cardiac stimulator 10. In this instance the cardiac stimulator 10 is connected to the ventricles of the heart and, as is customary, is housed under the skin in the abdominal area. The cardiac stimulator 10 must be replaced periodically, e.g., every 2–3 years. To do this an incision is made in the abdominal area adjacent the stimulator 10, the plug 20 detached from the cardiac stimulator 10 and attached to the new cardiac stimulator and the incision closed.

The electrical leads 14 and 16 are identical. Referring to FIGS. 2, 3 and 4 also, these electrical leads comprise three sections; an insulated electrical conducting section 22, a non-insulated electrical conducting section 24, and a lead-in securing section 26. The insulated electrical conducting section 22 is preferably spring helical wire comprising an electrical conducting wire, in this instance braided wire, coated with insulating material. The electrical conducting wire may be made of any electrical conductive material which is non-toxic to the animal or human. The selection of suitable electrical conductive material is a matter of choice within the ordinary skill of one in the art. The insulating material may be any plastic or other material which is non-toxic to the animal or human. The selection of suitable insulating material is also a matter of choice within the ordinary skill of one in the art. This spring helical wire will expand when tension is applied and return to its original length when the tension is released. The insulated electrical conducting section 22 is well known in the art and does not per se constitute a part of the present invention.

One end of the section 22 is attached by soldering or the like to the electrical plug 20 as illustrated in FIG. 1. The other end is attached to, or in this instance forms, the non-insulated electrical conducting section 24. In this instance the section 24 is merely the same as the section 22 with the exception that the insulating material has been removed from the electrical conducting wire.

The lead-in securing section 26 is connected to the non-insulated electrical conducting section 24 and comprises a substantially rigid helical member, in this instance a wire, preferably having a sharp point 28 at its end. The shape and longitudinal rigidity of the lead-in securing section 26 permit it to be attached to, and enhance its holding effect after attachment, a wall 30 of the heart 12 as illustrated in FIG. 2. Preferably, the lead-in securing section 26 is tapered toward the point 28 as illustrated in FIGS. 2, 3 and 4. However, a portion of reduced diameter will suffice for use with the insertion tool to be discussed hereinafter.

The lead-in securing section 26 may be made of any metal or plastic material which is non-toxic to the animal or human and connected by any means to the section 24. The selection of suitable material and the means by which they are connected are matters of choice within the ordinary skill of one in the art. Preferably, however, section 26 is made of an electrical conductive metal.

By way of example and to give perspective to the sizes of the electrical leads 14 and 16, the insulating electrical conducting section 22 is generally about 8–12 inches in length and has a diameter in the range of about 1/16 and ⅛ inch. The non-insulating electrical conducting section 24 has, in this instance, the same diameter as the section 22 and since it only comprises a few turns or less will have a length generally less than ⅛ inch. The lead-in securing section 26 preferably has its largest diameter equal to the diameter of the other sections and is generally in the range of about ⅛ and ¼ inch in length as a few turns are generally sufficient though less may be used.

Referring to FIG. 3 the electrical lead 14 is attached or secured to the heart 12 with an insertion tool indicated generally by reference numeral 32. The insertion tool 32 has an elongated shaft 34 having a bevelled portion 36, like the end of a screw driver, and a handle 38 at its respective ends. To prepare the electrical lead 14 for attachment to the heart, the bevelled end 36 of the insertion tool 32 is inserted between a turn in the helical wire of the conducting section 22, such as at point 40 illustrated in FIG. 3, and pushed into the electrical lead 14 until the bevelled end 36 engages and grips the tapered portion of the lead-in securing section 26. By way of illustration, the insertion tool 32 is about 12 inches in length and the shaft 34 has a diameter of about 0.05 inches, which is substantially less than the diameter of the insulated and non-insulated sections 22 and 24, respectively, of the electrical lead 14.

To prepare the heart for receiving the electrical lead, a small incision is made in the pericardium and epimyocardial fascia (not shown) of the heart to expose the heart muscle 30 to which the electrical lead 14 is secured. The insertion tool 32, while engaging and gripping the lead-in securing section 26, is rotated by hand to screw the lead-in securing section 26 into the heart muscle 30. As shown in FIG. 2, the lead-in securing section 26 is rotated sufficiently so that this section, as well as the entire non-insulated electrical conducting section 24 and some turns of the insulated electrical conducting section 22, are screwed in the heart muscle 30. The insertion tool 32 is then withdrawn from the lead 14 and this lead is securely fastened to the heart 12. As the electrical lead 14 is being screwed into the heart muscle care should be taken to rotate the entire electrical lead 14, such as by rotating the terminal connector plug 20, otherwise there will be a tendency of the electrical lead 14 to unwind when the tool 32 is removed and thus unscrew from the heart muscle 30.

After the electrical lead 14 has been securely attached to the ventricle of the heart 12, the other electrical lead 16 is securely attached thereto in a similar manner. There is, however, one significant variation. With the electrical lead 14 firmly implanted in the heart 12, one can no longer compensate for the tendency of the electrical lead 16 to wind up during insertion, and therefore unscrew when the hand tool 32 is released, by turning the plug 20 since that would cause the electrical lead 14 to be twisted and to tend undesirably to screw out of or further into the heart muscle 30. Therefore with the second electrical lead 16 the number of revolutions it will be screwed into the heart is predetermined and the electrical lead wrapped around the insertion tool 32, as illustrated in FIG. 4, in the opposite direction the same number of turns. For example, if it will require eight clockwise rotations to screw the electrical lead 16 into the heart muscle 30 the desired distance, then the electrical lead 16 is wrapped eight counterclockwise rotations around the insertion tool. In this manner the electrical lead 16, after attachment to the heart wall 30, is not under any force caused by twisting of the wire which would tend to screw it out of or further into the heart wall 30. As illustrated in FIG. 4, the electrical lead 16 requires clockwise rotations for insertion and therefore it has been wrapped in a counterclockwise manner around the shaft 34 of the tool 30.

A significant feature of the electrical leads of the present invention is that they may be secured to the heart through mediastinoscopy, for example, which is a less drastic surgical procedure than a thoracotomy. However, it will be understood that the electrical leads of the present invention may be utilized regardless of the surgical procedures employed to afford access to the heart.

Another important feature of the electrical lead of the present invention is that it causes less trauma to the heart than heretofore known techniques of attaching electrical leads. In addition to the general desirability of minimizing trauma to the heart for the well being of the patient, heart trauma plays an important part in heart pacing system. In the areas where the heart has been subjected to trauma scar tissue forms. Scar tissues do not conduct electricity. Therefore, the greater the area of scar tissue, the more current needed for the electric impulses to reach the receptive tissue of the heart. Increased current requires larger batteries or electricity generators and thus the size of the stimulator is increased. The larger the stimulator the more inconvenient it is for the body to carry it and the less chance of concealing it in the abdominal area of a human.

The non-insulated conducting section 24 affords another feature of the electrical lead of the present invention. The heart is continually in motion by virtue of its constant expansion and contraction, which places great stress upon the juncture between the substantially rigid lead-in securing section 26 and the section 24. If there should be any breakage it is most likely to occur at this juncture. Should this occur the exposed turns in section 24 assure that electricity will continue to be provided to the heart 30. It is anticipated of course, that the electrical leads 14 and 16 are screwed into the heart muscle 30 sufficiently so that there are least few turns of the section 22 in the heart muscle 30 also. The more turns that are embedded in the heart muscle, the stronger the attachment of the electrical lead to the heart.

It is preferred that the electrical leads 14 and 16 be screwed into the heart muscle so that they are positioned substantially tangential to the heart muscle and tend to run parallel with it, as illustrated in FIG. 2, rather than perpendicular thereto. It has been found that this substantially reduces the chances of the section 26 breaking off of the rest of the electrical lead.

FIG. 5 illustrates another electrical lead embodying the features of the present invention and indicated generally by reference numeral 50. The electrical lead 50 has an insulated electrical conducting section 22 and a non-insulating conducting section 24 identical to electrical leads 14 and 16. However, the lead-in securing section 52 comprises a hollow, tapered cylindrically-shaped member having a helical ridge 54 on its outer periphery which terminates at a sharp leading point 56. This electrical lead 50 is attached to the heart in the same manner as the leads 14 and 16 discussed hereinbefore and has all of the advantages of these leads also. However, it has the further advantage that it is unnecessary to cut the epi-myocardial fascia, as required when using the electrical leads 14 and 16 because of bunching or curling of the fascia during insertion.

Although it is preferred that the insulated and non-insulated electrical conducting sections 22 and 24, respectively, be made of spring helical wire, it will be understood that any other type of wire may also be used if sufficient slack is left to allow for the movement of the heart. Furthermore, though the section 24 is preferred it will be understood that it may be eliminated so long as the section 26 is made of electrically conductive material.

FIG. 6 illustrates another electrical lead embodying the features of the present invention and indicated generally by reference numeral 60 which combines two electrical leads 62 and 64 into a single lead. The electrical lead 62, as illustrated, is the same as the electrical leads 14 and 16 discussed hereinbefore, but it is to be understood that it may be the same as the electrical lead 50 also. The electrical lead 64 is the same as these leads 14, 16 and 50 without the lead-in securing sections and is wound within the spaces of the electrical lead 62. The non-insulated conductive section 66 of the lead 64 begins and terminates in back of the non-insulated section 68 of the electrical lead 62 to prevent a short circuit in the system. The electrical lead 60 is installed in the same manner as the electrical leads 14, 16 and 50 and inserted sufficiently so that the non-insulated conductive section 66 of the lead 64 is within the heart muscle. If the insulated and non-insulated electrical conducting sections of the leads 62 and 64 are not made of spring helical wire as illustrated in FIG. 6, the lead 64 is twisted or wrapped about the lead 62, the non-insulated section of the lead 64 terminating adjacent to, but spaced from, the non-insulated section of the lead 62. Minimization of trauma to the heart and the elimination of the problem discussed in connection with FIG. 4 are some of the features afforded by this embodiment.

FIG. 7 illustrates another embodiment of a cardiac stimulator system. In this instance each electrical lead 70 is connected to its own electrical terminal connector plug 72 and may be separately connected and disconnected to the cardiac stimulator 74. This eliminates the special procedures discussed in connection with FIG. 4 and permits each electrical lead 70 to be installed in the same manner as electrical lead 14 discussed hereinbefore.

It has further been discovered that in the type of electrical leads discussed herein there is generally a small space between the electrical conducting wire and the insulating material which creates a capillary action after the electrical lead has been attached to the heart and undesirably draws blood from the heart muscle into the insulating material. It has been found that this may be obviated by inserting the ends of the electrical leads into a suitable sealing material, such as epoxy resin or the like. The capillary action will draw the sealing material between the insulating material and the electrical wire and, upon hardening, seal off the end of the electrical lead between the wire and coating.

Where the human heart block is a S-A node blockage, the condition may be corrected by attaching the cardiac stimulator directly to the atrium. Any of the procedures discussed hereinbefore may be used.

The lack of blood vessels around the human heart is referred to as ischemia and causes coronary insufficiency. The build-up of blood vessels around the heart may be effected by attaching a cardiac stimulator by any of the methods discussed hereinbefore directly to the atrium. In this manner the heart may be paced at a faster rate than it normally operates and will effect continual mild exercise of the heart. The development of more blood vessels about the heart resists coronary insufficiency and lessens the likelihood of a heart attack.

While the embodiments described herein are at present considered to be preferred it will be understood that various modifications and improvements may be made therein and it is intended to cover in the appended claims all such modifications and improvements as fall within the true spirit and scope of the invention.

What is claimed is:

1. An electrical lead that may be screwed into an organ which comprises an insulated electrical conducting section and a lead-in securing section with a longitudinally rigid helical member which may be screwed into the organ.

2. The electrical lead of claim 1 including a non-insulated electrical conducting section between said insulated electrical conducting section and said lead-in securing section.

3. The electrical lead of claim 2 wherein said insulated and non-insulated electrical conducting sections comprise a spring helical wire with insulation and without insulation, respectively.

4. The electrical lead of claim 1 wherein said helical member has a free end and is tapered in diameter toward said free end.

5. The electrical lead of claim 1 wherein said helical member is electrically conductive and electrically connected to said insulated electrical conducting section.

6. An electrical lead that may be screwed into an organ which comprises a first electrical lead and a second electrical lead, said first electrical lead comprising an insulated electrical conducting section and a lead-in securing section with a longitudinally rigid helical member which may be screwed into the organ, the second electrical lead comprising an insulated electrical conducting section and a non-insulated electrical conducting section, said second electrical lead being wrapped about the insulated conducting section of said first electrical lead.

7. The electrical lead of claim 6 wherein said first electrical lead includes a non-insulated electrical conducting section between the insulated electrical conducting section and the lead-in securing section.

8. An electrical lead for a cardiac stimulator which comprises a first electrical lead and a second electrical lead, said first electrical lead comprising an insulated electrical conducting section, a lead-in securing section including a longitudinally rigid, sharply pointed helical member which may be screwed into the heart, and a non-insulated electrical conducting section between said other sections, said second electrical lead comprising an insulated electrical conducting section and a non-insulated electrical conducting section, said insulated and non-insulated electrical sections of said first and second electrical leads being made of spring helical wire with and without insulation, respectively, said second electrical lead being wound within the spaces of the insulated electrical conducting section of said first electrical lead and having its non-insulated section adjacent to and spaced from the non-insulated section of said first electrical lead.

9. A method of attaching an electrical lead of a cardiac stimulator to a heart which comprises utilizing an electrical lead which may be screwed into the heart, providing access to the heart through mediastinoscopy, and screwing the electrical lead into the heart for attachment thereto.

10. A method of attaching an electrical lead of a cardiac stimulator to a heart which comprises obtaining access to the heart and screwing a free end of the electrical lead into the heart.

11. The method of claim 10 wherein an insertion tool is utilized to grip said free end of said electrical lead and rotated to screw the electrical lead into the heart.

12. A method of attaching an electrical lead of a cardiac stimulator system to the heart, said electrical lead comprising an insulated electrical conducting section of spring helical wire and a lead-in securing section, comprising placing an insertion tool into said spring helical wire of the electrical conducting section and extending said insertion tool through said spring helical wire until it engages said lead-in securing section of said electrical lead, obtaining access to the heart, screwing the lead-in securing section into the heart with said insertion tool and withdrawing said insertion tool from said electrical lead.

13. The method of claim 12 wherein said electrical lead has a non-insulated electrical conducting section between said insulated conducting section and said lead-in securing section and said electrical lead is screwed into the heart so that said non-insulated electrical conducting section is also in the heart.

14. The method of claim 12 wherein said electrical lead is the first of two similar electrical leads attached to a terminal connector plug disconnectably attached to a stimulator, including after said first electrical lead has been attached to said heart the second electrical lead is wrapped about an insertion tool the number of times said second electrical lead is to be screwed into the heart, said second electrical lead being wrapped about said insertion tool in the opposite direction in which it is screwed into the heart, placing the insertion tool into the spring helical wire of the electrical conducting section of the second electrical lead and extending said insertion tool through said spring helical wire until it engages the lead-in securing section, screwing the lead-in securing section of the second electrical lead into the heart with said insertion tool and withdrawing said insertion tool from said electrical lead.

15. An electrical lead that may be screwed into an organ which comprises an insulated electrical conducting section and a lead-in securing section with a hollow member having a helical thread about its periphery which may be screwed into the organ.

16. The electrical lead of claim 15 wherein said helical member has a free end and is tapered in diameter toward its free end.

17. The electrical lead of claim 15 wherein said hollow member is electrically conductive and electrically connected to said insulated electrical conducting section.

18. An electrical lead for a cardiac stimulator which comprises an insulated electrical conducting section and a lead-in securing section with a longitudinally rigid helical member which may be screwed into the heart.

19. An electrical lead for a cardiac stimulator that may be screwed into a heart which comprises an insulated electrical conducting section, a non-insulated electrical conducting section and a lead-in securing section, and non-insulated electrical conducting section being between said other sections, the insulated electrical conducting section and the non-insulated electrical conducting section comprising a spring helical wire with and without insulation, respectively, said non-insulated electrical conducting section comprising no more than a few turns of said non-insulated spring helical wire, said lead-in securing section comprising an electrically conductive, longitudinally rigid, sharply pointed helical wire.

20. The electrical lead of claim 19 including terminal connector means to attach it to a cardiac stimulator.

21. An electrical lead that may be screwed into an organ which comprises a hollow insulated electrical conducting section and a substantially coaxial lead-in securing section with a longitudinally rigid helical member which may be screwed into the organ, said conducting section and said securing section being alignable along a substantially straight line.

22. An electrical lead for a cardiac stimulator which comprises a hollow insulated electrical conducting section and a substantially coaxial lead-in securing section with a longitudinally rigid helical member which may be screwed into the heart, said conducting section being alignable along a substantially straight line.

23. In a body implantable electrode assembly that includes a flexible insulated conductor projecting from a connector and wherein the distal end of the conductor is adapted for attachment to a body organ, the improvement which comprises:
   a. a conductor having its uninsulated distal end region formed as a rigid helix, and
   b. key engageable means on at least one convolution intermediate the ends of the rigid helix, whereby a slender key means that is admitted coaxially of the rigid helix may engage the key engageable means for screwing the helix into an organ.

24. The invention set forth in claim 23 wherein:
   a. said conductor comprises a flexible wire cable, and
   b. at least one convolution of said cable which is next in the proximal direction from said rigid distal end is uninsulated.

25. An electrical lead for attachment to a body organ which comprises:
   a. an insulated electrical conducting section;
   b. a non-insulated electrical conducting section electrically connected to said insulated electrical conducting section; and
   c. a sutureless securing means to hold said insulated electrical conducting section in electrical contact with said body organ, said sutureless securing means including means which extend into and attach to said body organ upon rotation of said sutureless securing means into said body organ to attach said electrical lead to said body organ.

* * * * *